US012788239B2

(12) United States Patent
Khanna et al.

(10) Patent No.: US 12,788,239 B2
(45) Date of Patent: Nov. 10, 2026

(54) SYSTEMS AND METHODS FOR CORRECTING AND OPTIMIZING A VISUAL FIELD

(71) Applicant: Mayo Foundation for Medical Education and Research, Rochester, MN (US)

(72) Inventors: Cheryl L. Khanna, Austin, MN (US); Raymond Iezzi, Rochester, MN (US); Jane M. Matsumoto, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 275 days.

(21) Appl. No.: 18/293,106

(22) PCT Filed: Aug. 1, 2022

(86) PCT No.: PCT/US2022/039012
§ 371 (c)(1),
(2) Date: Jan. 29, 2024

(87) PCT Pub. No.: WO2023/009886
PCT Pub. Date: Feb. 2, 2023

(65) Prior Publication Data

US 2024/0374131 A1 Nov. 14, 2024

Related U.S. Application Data

(60) Provisional application No. 63/227,470, filed on Jul. 30, 2021.

(51) Int. Cl.
*A61B 3/024* (2006.01)
*A61B 3/00* (2006.01)

(52) U.S. Cl.
CPC ............ *A61B 3/024* (2013.01); *A61B 3/0025* (2013.01)

(58) Field of Classification Search
CPC .............................. A61B 3/024; A61B 3/0025
See application file for complete search history.

(56) References Cited

U.S. PATENT DOCUMENTS

2002/0024634 A1 2/2002 Fink et al.
2019/0066369 A1 2/2019 Peng
2025/0295303 A1* 9/2025 Khanna .................. A61B 3/024

FOREIGN PATENT DOCUMENTS

EP 2869239 A2 5/2015
WO 2021043980 A1 3/2021

OTHER PUBLICATIONS

Berezina, T. et al., Peripheral Visual Field Thresholds Using Humphrey Field Analyzer Program 60-4 in Normal Eyes, European Journal of Ophthalmology, 2011, 21(4):415-421.

(Continued)

*Primary Examiner* — James C. Jones
(74) *Attorney, Agent, or Firm* — Quarle & Brady LLP

(57) ABSTRACT

Described herein is a system and method for correcting a visual field of a subject using a predicted visual field that includes visual field defects from facial contours of the subject. In an embodiment. the predicted visual field may be determined using a three-dimensional (3D) reconstruction of the face of the subject which may be generated from a two-dimensional (2D) image of the subject using a convolution neural network. A system and method for optimizing a head turn angle of a subject for determining a visual field of a subject is also described herein. An optimal head turn angle may be determined using the 3D reconstruction of the face of the subject. In some embodiments, after the visual field is maximized with positioning of the head. residual (Continued)

facial contour induced defects can be predicted and a final corrected field can be generated.

6 Claims, 15 Drawing Sheets

(56) References Cited

OTHER PUBLICATIONS

Chehade, J. et al., Correlation Between 60-4 Visual Field Defects and Facial Imaging, American Society of Cataract and Refractive Surgery, May 3, 2019, pp. 1-12.

Chehade, J. et al., Correlation of Facial Anatomy and 60-4 Visual Field Defects in Healthy Subjects, American Society of Cataract and Refractive Surgery, May 3, 2019, 2 pages.

Crounse, K. et al., Methods for Image Processing and Pattern Formation in Cellular Neural Networks: A Tutorial, IEEE Transactions on Circuits and Systems I: Fundamental Theory and Applications, 1995, 42(10):583-601.

Eperjesi, F., Qualitative Visual Field Analysis, Optician, Dec. 3, 2010, pp. 14-20.

Feng, Y. et al., Joint 3D Face Reconstruction and Dense Alignment with Position Map Regression Network, In Proceedings of the European Conference on Computer Vision (ECCV), 2018, pp. 534-551.

Glittenberg, C. et al., Modeling the Effect of Facial Topographies Upon the Visual Field of Humans and Primates, Ophthalmic and Physiological Optics, 2009, 29(5):509-517.

Hood, D. et al., Challenges to the Common Clinical Paradigm for Diagnosis of Glaucomatous Damage with OCT and Visual Fields, Investigative Ophthalmology & Visual Science, 2018, 59(2):788-791.

Jourabloo, A. et al., Large-Pose Face Alignment Via CNN-Based Dense 3D Model Fitting, In Proceedings of the IEEE Conference on Computer Vision and Pattern Recognition, IEEE, 2016, pp. 4188-4196.

Kingman, S., Glaucoma is Second Leading Cause of Blindness Globally, Bulletin of the World Health Organization, 2004, 82:887-888.

Odden, J. et al., Evaluation of Central and Peripheral Visual Field Concordance in Glaucoma, Investigative Ophthalmology & Visual Science, 2016, 57(6):2797-2804.

Patton, N. et al., Pupillary Anomaly Masquerading as a Glaucomatous Visual Field Defect: A Case Report, BMC Ophthalmology, 2004, 4:6, 2 pages.

Racette, L. et al., External Obstructions Blocking Stimuli from Reaching the Retina, Visual Field Digest: A Guide to Perimetry and the Octopus Perimeter, 8th ed., Haag-Streit AG, 2019, p. 43.

Rutkowski, P. et al., The Peripheral and Central Humphrey Visual Field—Morphological Changes During Aging, BMC Ophthalmology, 2017, 17:127, pp. 1-7.

Yamao, S. et al., Effects of Head Tilt on Visual Field Testing with a Head-Mounted Perimeter Imo, PLoS ONE, 2017, 12(9):e0185240, pp. 1-11.

PCT International Search Report and Written Opinion, PCT/US2022/039012, Oct. 21, 2022, 12 pages.

* cited by examiner

604

53, 75, 75, 93], 'text': ['', '', '', '', 'Threshold', '(dB)', '', '269', '364', '', '2', '5', '19120', '23', '22', '
', '5', '19', '25', '25, '287', '26', '28', '29', '25', '25', '', '16, '24', '26', '32', '28', '25', '', '20', '26'
, '30', '31', '28', '25', '', '60 ', '60 ', '', '21', '26', '28', '33', '30–39', '', '20', '26', '28', '33.', '3130',
'', '20', '26', '31, '30732', '30', '32', '28', '', '10', '21', '27', '29730', '30', '29', '26', '', '26', '', '386', '20',
24], '26', '27', '475']}

606

FIG. 6C

SYSTEMS AND METHODS FOR CORRECTING AND OPTIMIZING A VISUAL FIELD

BACKGROUND

Certain ocular disorders, such as glaucoma, retinitis pigmentosa, optic neuropathies due to injuries, or toxicity from medications (e.g., corticosteroids, antibiotics, antineoplastic and antiarrhythmics), result in peripheral visual defects. Proper assessment of peripheral visual defects has broad implications across medical specialties. Ideally, an individual's complete visual field would be performed from the central to far periphery in a single field for diseases affecting the visual field to allow accurate assessment of disease severity and progression.

Glaucoma is a major cause of irreversible blindness worldwide with significant quality of life implications. As such early detection of glaucoma is critical in controlling visual deterioration and preserving visual function. In glaucoma, loss of retinal ganglion cells leads to loss of peripheral vision. Functional assessment for measuring glaucoma progression includes visual field testing. Visual field can be assessed with 24-2, 30-2, and 60-4 testing patterns, which vary in the degree of deviation from the central axis measured and number of testing points considered. Notably, central vision can be assessed with 24-2 and 30-2 field patterns; however, peripheral vision beyond 30 degrees of the central visual field axis are assessed with a 60-4 threshold.

The central visual field is more commonly assessed in clinical practice for tracking glaucoma progression. This partly stems from wide variability and unclear appropriate thresholds in 60-4 visual field of healthy control subjects, potentially due to differences in point sensitivity and the potential impact of facial structure. Additionally, in moderate to severe cases of glaucoma, peripheral visual field defects accompany central visual field defects. Unfortunately, in early stages of glaucoma, central and peripheral visual field loss may not be correlated; peripheral defects may manifest in the absence of central field defects. In fact, 11-17% of patients with glaucoma may have peripheral visual field defects in the absence of central visual field defects. Detecting visual field defects associated with glaucoma in the peripheral region may enable earlier detection and treatment of the disease.

Facial contours (e.g., nose, cheeks, eyebrows, etc.) can impact far peripheral visual field results when utilizing, for example, a 60-4 testing pattern. The impact of facial structure on field defects may complicate identification of pathological peripheral field defects. Specifically, prominent facial structures may obscure areas of the peripheral field which would otherwise be useful in disease monitoring. Both central and peripheral visual defects have independent diagnostic value and impact on quality of life, with peripheral defects increasing fall risk and alterations in balance. Thus, attainment of an accurate visual field and optimizing strategies for distinguishing facial contour-dependent field defects from pathological defects is paramount for detection of ocular disease progression.

Thus, there remains a need for systems and methods for distinguishing peripheral visual field defects related to ocular pathology from peripheral visual field defects related to facial structures (or contours) and for correcting or compensating for visual field defects caused by facial structures to maximize the visual field. Mapping the visual field from mild to severe disease and correcting for individual variation of facial contour is critical to accurately diagnose and follow disease progression.

SUMMARY OF THE DISCLOSURE

In accordance with an embodiment, a method for determining a visual field of a subject includes providing a two-dimensional (2D) image of a face of the subject to a convolutional neural network (CNN), generating, using the CNN, a three-dimensional (3D) reconstruction of the face of the subject based on the 2D image of the face of the subject, determining a plurality of intersect angles between a visual axis and a plurality of circumferential points on the 3D reconstruction of the face of the subject, identifying a set of circumferential points with a corresponding intersect angle less than a predetermined angle, generating a predicted visual field for the subject based on the set of circumferential points with a corresponding intersect angle less than the predetermined angle, retrieving an acquired visual field for the subject, the acquired visual field acquired from a subject using a visual field system, generating a corrected visual field based on the predicted visual field for the subject and the acquired visual field for the subject, and displaying the corrected visual field for the subject.

In accordance with an embodiment, a system for determining a visual field of a subject includes a three dimensional (3D) reconstruction module configured to receive a two-dimensional (2D) image of a face of the subject and comprising a convolutional neural network configured to generate a 3D reconstruction of the face of the subject based on the 2D image of the face of the subject, a visual field prediction module coupled to the 3D reconstruction module and configured to generate a predicted visual field for the subject based on the 3D reconstruction of the face of the subject; and a visual field correction module coupled to the visual field prediction module and configured to receive the acquired visual field for the subject, the visual field correction module further configured to generate a corrected visual field based on the predicted visual field for the subject and the acquired visual field of the subject.

In accordance with an embodiment, a method for optimizing a head turn angle for determining a visual field of a subject includes providing a two-dimensional (2D) image of a face of the subject to a convolutional neural network (CNN), generating, using the CNN, a three-dimensional (3D) reconstruction of the face of the subject based on the 2D image of the face of the subject, determining a plurality of intersect angles between a visual axis and a plurality of circumferential points on the 3D reconstruction of the face of the subject, identifying a smallest of the plurality of intersect angles, determining an optimal head turn angle based on the smallest of the plurality of intersect angles, and storing the optimal head turn angle.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 6A-6E illustrate an example numerical method for correction of an acquired visual field in accordance with an embodiment;

DETAILED DESCRIPTION

Figure 1:
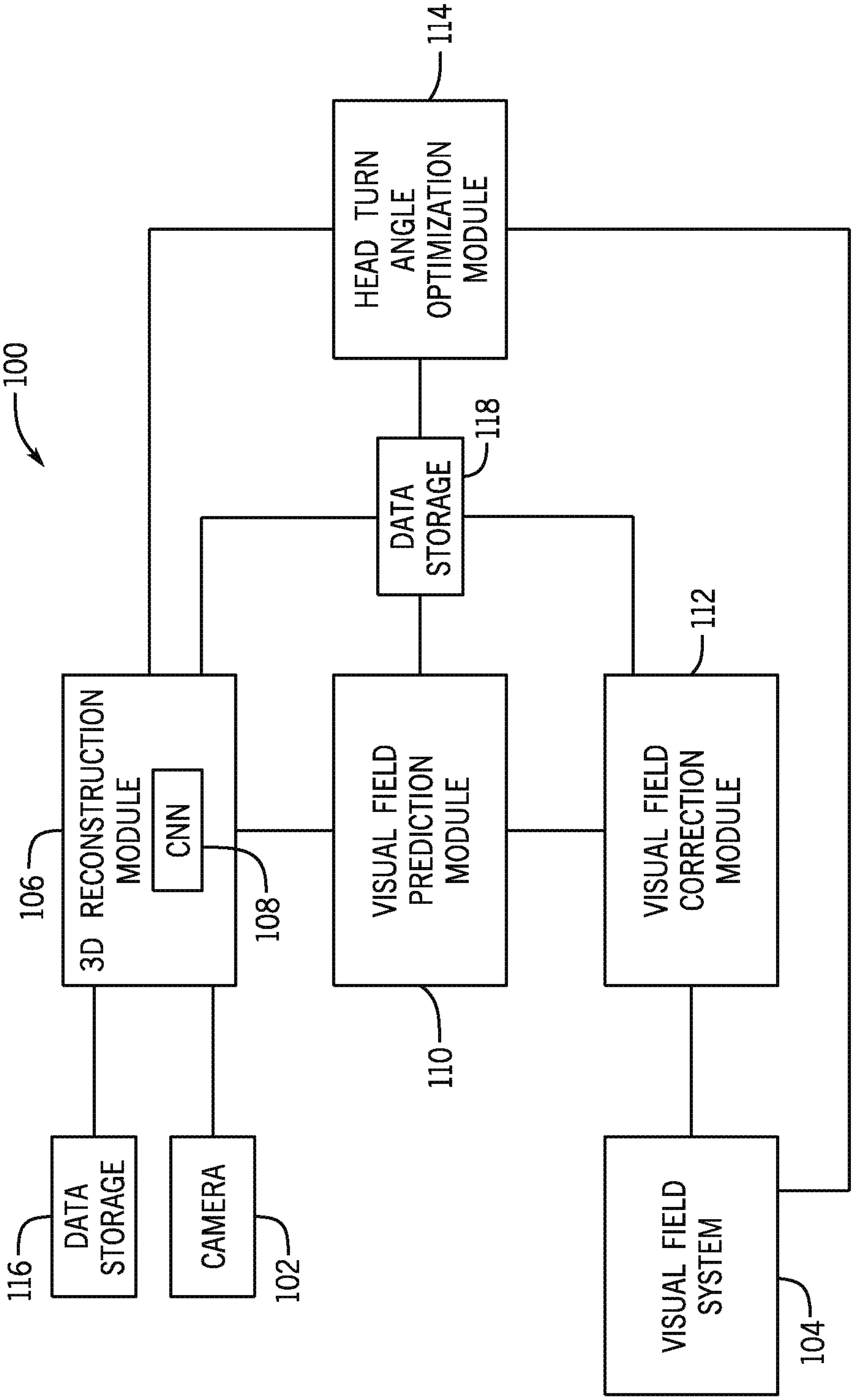
FIG. 1 is a block diagram of a system for correcting and optimizing a visual field of a subject in accordance with an embodiment.

The present disclosure describes systems and methods for correcting and optimizing a visual field of a subject. In patients with ocular pathology, it is important to determine what visual field defects are due to ocular pathology and what visual field defects are due to variations in facial structure (or facial contour). The facial contour of a subject may be influenced by factors such as age, race and gender. In some embodiments, a system and method for determining a visual field of a subject predicts what visual field defects identified in a visual field of the subject are from facial contour and corrects an acquired visual field of the subject to remove the visual field defects from facial contour from the acquired visual field. Accordingly, the corrected acquired visual field may have visual field defects from ocular pathology. The corrected visual field may advantageously allow a provider to focus on visual field changes associated with the ocular disease such as, for example, glaucoma, retinitis pigmentosa, diabetic retinopathy, and optic neuropathies due to injuries, as well as visual field changes associated with toxicity from medications. The corrected visual field may be used to, for example, measure a patient's visual field, to diagnose ocular disease, to determine the effect of treatment on the disease, and to monitor and accurately plot progression of an ocular disease including, but not limited to, glaucoma. In some embodiments, a predicted visual field may be generated using a three-dimensional (3D) reconstruction of the face of a subject which is generated from a two-dimensional (2D) image (e.g., a photograph) of the face of the subject using a convolutional neural network (CNN). The predicted visual field predicts where visual field defects can occur based on the facial contour of a subject. In some embodiments, a corrected visual field may be generated by subtracting the predicted visual field from an acquired (or actual) visual field of the subject. In some embodiments, a numerical correction method may be used to generate the corrected visual field. Advantageously, the visual field defects caused by facial contour may be separated and distinguished from the visual field defects caused by ocular pathology.

As mentioned above, the facial contour of a subject may be influenced by factors such as age, race and gender. In some embodiments, the prediction of visual field defects in a subject's visual field that are caused by facial structure or contour may be used to identify differences in facial contours based on factors such as, for example, age, race and gender. For example, the prediction of facial contour related visual field defects can illustrates differences in facial contour between males and females (i.e., less facial contour related visual contour defects in women) and differences in facial contour between Asian and non-Asian subjects (i.e., less facial contour related visual field defects in Asian subjects). The differences in facial contour related visual field defects based on factors such as race and gender may be caused, for example, by a more prominent nasal contour being more common in subjects in one of the groups defined by, for example, race and gender. The identified differences in facial contour visual field defects based on, for example, age, race and gender, may be used to develop a normative database or correction factor for visual fields such as, for example, 60-4 fields or 0 to 60 degree fields.

Various ocular conditions (e.g., glaucoma) can cause visual field defects in the peripheral region. To preserve the visual field in patients with an ocular condition (e.g., glaucoma), it is important to accurately track all of the visual field, including the peripheral field. Generally, 24-2 or 30-2 visual fields are used for monitoring ocular diseases such as glaucoma, however, these visual fields will frequently miss visual field defects outside of the central 30 degrees of a patients visual field. Vision beyond 30 degrees (e.g., the peripheral 30 to 60 degrees) may be assessed with a far peripheral visual field, for example, a 60-4 visual field, however, 60-4 visual fields are not routinely done for numerous reasons including peripheral visual field defects caused by facial anatomy which can result in an incorrect diagnosis. The disclosed systems and methods that can be used to distinguish peripheral visual field defects related to ocular pathology from peripheral visual field defects related to facial structures and contours, and to correct for the visual field defects caused by facial structures and contours can allow for use of far peripheral fields (e.g., a 60-4 visual field) to diagnose and follow progression of an ocular disease such as glaucoma. Accordingly, far peripheral visual fields, e.g., a 60-4 visual field, may advantageously be included in the standard of care for routine testing for patients with an ocular condition such as glaucoma.

Visual field defects caused by facial contour of a subject may be altered, for example, by turning the subject's head relative to a vertical axis towards (i.e., temporally) or away from (i.e., nasally) the eye being tested using a visual field system. In some embodiments, a system and method for optimizing a head turn angle for determining a visual field of a subject may determine an optimal head turn angle for the subject using a three-dimensional (3D) reconstruction of the face of a subject which is generated from a two-dimensional (2D) image (e.g., a photograph) of the face of the subject using a CNN. The optimal head turn angle may advantageously be used to optimize viewing of the entire visual field of the subject. By positioning a subject's head at the optimal angle in a visual field machine for performing a visual field test, it may be possible to more completely and accurately map the subject's peripheral vision. For each individual subject, the optimal head turn angle to view the maximum visual field may be different. The optimal head turn may be used to minimize facial contour visual field defects, however, the optimal head turn may not completely eliminate these defects. Therefore, in some embodiments, residual facial contour visual field defects may be accounted for after ideal head positioning using the system and method for identifying and correcting facial contour visual field defects. Mapping the entire visual field from central to peripheral and correcting for facial contour visual field defects is important for diagnosis, identifying progression of disease of patients with mild to severe ocular pathology, and identifying response to treatment in patients with mild to severe ocular pathology.

FIG. 1 is a block diagram of a system for correcting and optimizing a visual field of a subject in accordance with an embodiment. The system 100 includes a camera 102, a visual field system 104, a three-dimensional (3D) reconstruction module 106 that includes a convolutional neural network (CNN) 110, a visual field prediction module 110, a visual field correction module 112, and a head turn angle optimization module 114. In various embodiments, elements of system 100 may be implemented in the same device. In other embodiments, various elements are implemented in different locations or devices and may be in signal communication via wired or wireless connections. For example, the 3D reconstruction module 106, visual field prediction module 110, visual field correction module 112, and head turn optimization module 114 may be implemented as part of the visual field system 104 (e.g., using a processor), or may be implemented on a processor of a separate computer system (e.g., a computer system such as computer system 900 described further below with respect to FIG. 9).

As mentioned, the 3D reconstruction module 106, visual field prediction module 110, visual field correction module 112, and head turn optimization module 114 may be implemented on a processor (e.g., one or more processor devices). In some implementations, the processor may be included in any general-purpose computing system or device, such as a personal computer, workstation, cellular phone, smartphone, laptop, tablet, or the like. The processor may include any suitable hardware and components designed or capable of carrying out a variety of processing and control tasks, including, for example, steps for determining a corrected visual field of a subject or determining an optimized head turn angle for determining a visual field of a subject. For example, the processor may include a programmable processor or combination of programmable processors, such as central processing units (CPUs), graphics processing units (GPUs), and the like. In some implementations, the processor may be configured to execute instructions stored in a non-transitory computer readable-media. In this regard, the processor may be any device or system designed to integrate a variety of software, hardware, capabilities and functionalities. Alternatively, and by way of particular configurations and programming, the processor may be a special-purpose system or device. For instance, such special-purpose system or device may include one or more dedicated processing units or modules that may be configured (e.g., hardwired, or pre-programmed) to carry out steps, in accordance with aspects of the present disclosure.

The camera 102 may be any standard camera known in the art that may be used to acquire a two-dimensional (2D) image (i.e., a photograph) of a subject. In particular, the camera 102 may be used to acquire one or more 2D images of a face of a subject. In an embodiment, the 2D image can be an RGB image. The 2D image(s) of the face of the subject acquired by the camera 102 may be stored in data storage (or memory) 116, for example, data storage of the camera 102, the visual field system 104, or other computer system (e.g., storage device 916 of computer system 900 shown in FIG. 9). In some embodiments, the 2D images of the face of the subject may be stored as high-resolution JPEG images. The visual field system 104 may be any visual field system that may be configured to perform different types of visual field tests that each measure various degrees of peripheral vision including, but not limited to, a 10 degree visual field (e.g., 10-2), a 30 degree visual field (30-2) and a 60 degree visual field (60-4), or a combination of fields, including central, mid peripheral, and/or far peripheral. The visual field tests may be performed on a subject by the visual field system 104 using known methods. The acquired visual field may be for a right eye of the subject or a left eye of the subject. The visual field of a subject acquired using the visual field system 104 may be stored in data storage (or memory), for example, data storage of the visual field system 104, or other computer system (e.g., storage device 916 of computer system 900 shown in FIG. 9).

The 3D reconstruction module 106 may be configured to receive one or more 2D images (i.e., photographs) of a face of a subject from the camera 102. The 2D image of the face of a subject may be, for example, transmitted from the camera 102 via a communication link or retrieved from data storage (or memory) 116. The 3D reconstruction module 106 includes a convolutional neural network (CNN) 108 that may be configured to generate a 3D reconstruction of the face of the subject using the 2D image (or images) of the face of the subject as discussed further below with respect to FIG. 2. The CNN may be trained using known or developed methods. The 3D reconstruction of the face of the subject may be stored in data storage (or memory) 118, for example, data storage of the visual field system 104, or other computer system (e.g., storage device 916 of computer system 900 shown in FIG. 9). The 3D reconstruction of the face of the subject generated by the 3D reconstruction module 106 may be provided to the visual field prediction module 110 coupled to the 3D reconstruction module 106. The visual field prediction module 110 may be configured to generate a predicted visual field of the subject indicating predicted visual field defects from facial contours (or structures) of the subject such as, for example, nose, cheeks, eyebrows, etc. The facial contour of a subject may be influenced by factors such as age, race and gender. The predicted visual field may be generated using the 3D reconstruction of the face of the subject as discussed further below with respect to FIG. 2. In some embodiments, the predicted visual field can be a 60-4 visual field, although it should be understood that other types of visual fields may be used for the predicted visual field. The predicted visual field may be for a right eye of the subject or a left eye of the subject. The predicted visual field for the subject may be stored in data storage (or memory) 118, for example, data storage of the visual field system 104, or other computer system (e.g., storage device 916 of computer system 900 shown in FIG. 9).

The visual field correction module 112 may be coupled to the visual field prediction module 110. The predicted visual field for the subject may be provided to the visual field correction module 112. In addition, the visual field correction module 112 may be configured to receive an acquired visual field for the subject from the visual field system 104. The acquired visual field for the subject may be, for example, transmitted from the visual field system 104 via a communication link or retrieved from data storage (or memory). In some embodiments, the acquired visual field may be a central, mid peripheral, far peripheral, or combination visual field. The visual field correction module 112 may be configured to generate a corrected visual field for the subject. In some embodiments, the corrected visual field may be generated by subtracting the predicted visual field for the subject from the acquired visual field for the subject as discussed further below with respect to FIG. 2. In some embodiments, the corrected visual field may be generated using a numerical correction method as discussed further below with respect to FIG. 2. Accordingly, the visual field defects from facial contours can advantageously be removed from the acquired visual field. The corrected visual field may be for a right eye of the subject or a left eye of the subject. The corrected visual field for the subject may be stored in data storage (or memory) 118, for example, data storage of the visual field system 104, or other computer system (e.g., storage device 916 of computer system 900 shown in FIG. 9). In some embodiments, the corrected visual field for the subject may be displayed on a display, for example, a display of visual field system 104, or other computer system (e.g., display 918 of computer system 900 shown in FIG. 9).

The head turn angle optimization module 114 may be coupled to the 3D reconstruction module 106 and the visual field system 104. The head turn angle optimization module 114 may be configured to determine an optimal head turn angle for a subject to maximize the visual field of the subject acquired, for example, using the visual field system 104. In an embodiment, by positioning the subject's head in the visual field system 104 at the optimal head turn angle when acquiring a visual field, the visual field defects caused by facial contour can be minimized as discussed further below with respect to FIG. 7.

Figure 2:
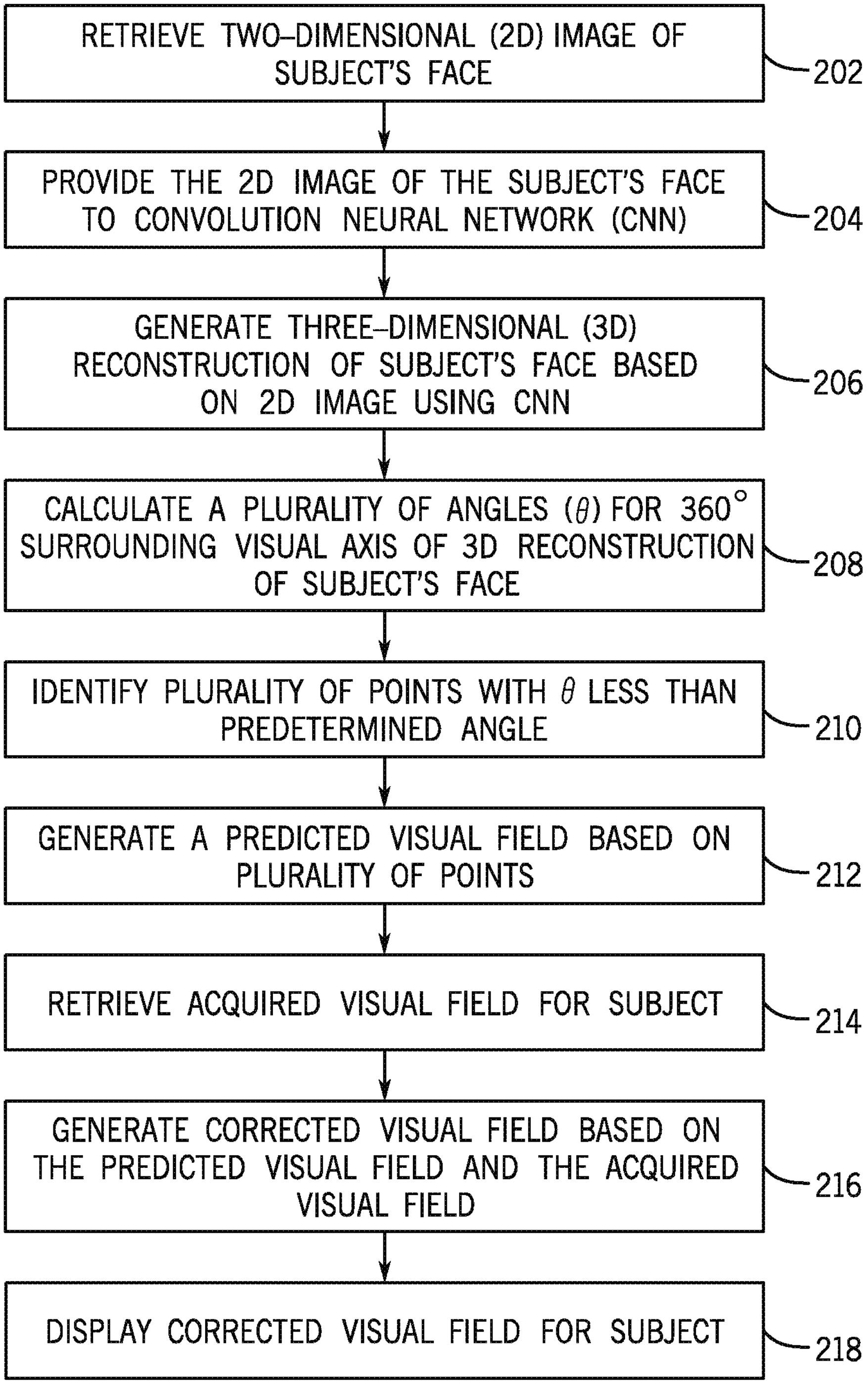
FIG. 2 illustrates a method for determining a corrected visual field for a subject with facial contour visual field defects in accordance with an embodiment.

FIG. 2 illustrates a method for determining a corrected visual field for a subject without facial contour visual field defects in accordance with an embodiment. The process illustrated in FIG. 2 is described below as being carried out by the system 100 for correcting and optimizing a visual field of a subject as illustrated in FIG. 1. Although the blocks of the process are illustrated in a particular order, in some embodiments, one or more blocks may be executed in a different order than illustrated in FIG. 2, or may be bypassed.

Figure 3A:
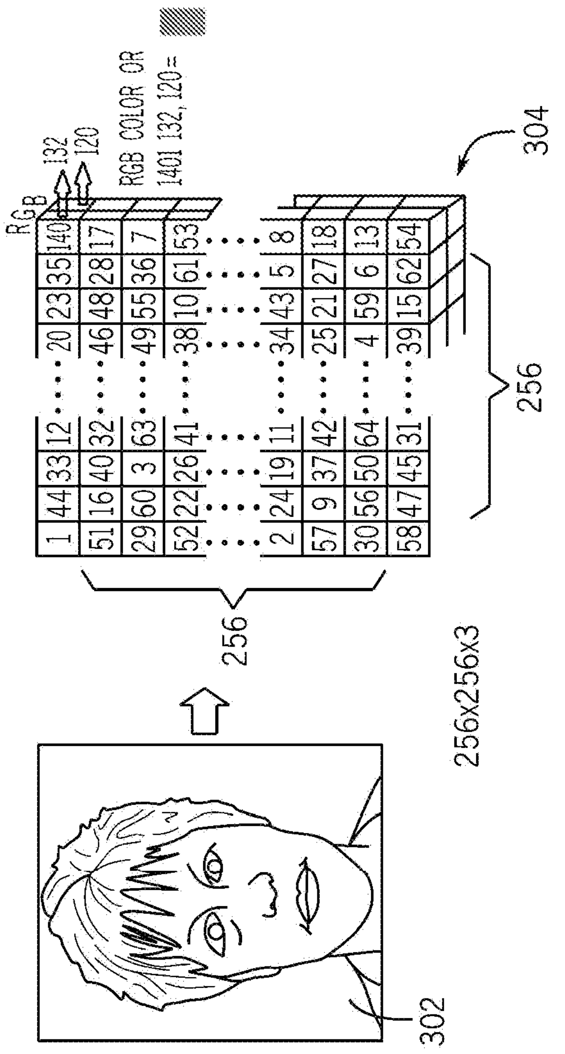
FIG. 3A illustrates a representative two-dimensional (2D) image of a subject's face projected onto a UV map in accordance with an embodiment.
Figure 3B:
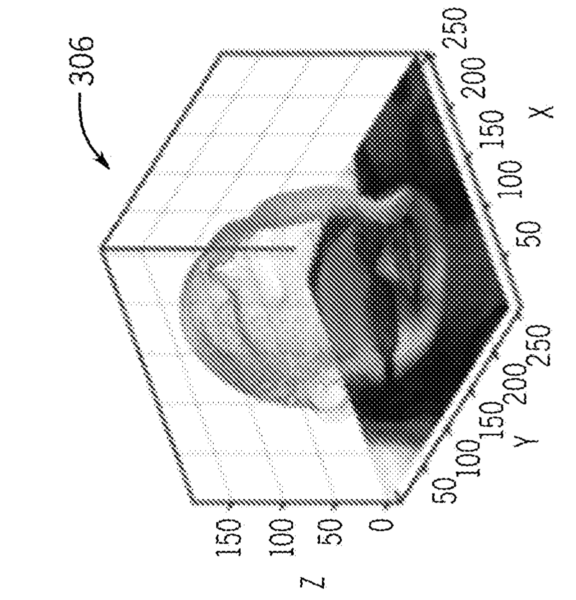
FIG. 3B illustrates an example 3D reconstruction of a face of a subject in accordance with an embodiment.

At block 202, a two-dimensional (2D) image of a face of a subject may be retrieved, for example, from a camera 102 or data storage 116. In some embodiments, the 2D image of the face of a subject can be an RGB image. In some embodiments, the 2D image of the face of the subject may be a high-resolution JPEG image. At block 204, the 2D image of the face of the subject may be provided to a 3D reconstruction module 106 that includes a trained convolutional neural network (CNN) 108. As mentioned, the CNN 108 may be trained using known methods. In some embodiments, the 2D image of the face of the subject may be pre-processed (e.g., using the 3D reconstruction module 106) to resize the 2D image to a predetermined size, one example being 256×256 pixels. At block 206, a 3D reconstruction of the subject's face may be generated based on the 2D image of the face of the subject and using the CNN 108. In some embodiments, a UV position map may be used as the presentation of 3D face structures. The UV position map may be created using, for example, the 3D reconstruction module 106. From the 2D image, X and Y coordinates may be placed into a UV position map which is a 2D image representation of the 3D positions. FIG. 3A illustrates an example two-dimensional (2D) image of a face of a subject projected onto a UV map in accordance with an embodiment. In FIG. 3A, the 2D image 302 of a face of a subject may be sized, for example, to 256×256×3, namely, 256 pixels, 256 pixels and 3 RED, BLUE, GREEN values for example, 256×256×5,12,15, or another predetermined size. A UV position map 304 for the 2D image 302 is shown. The 2D image 302 may be projected onto the UV position map 304 with $X_i$, $Y_i$ coordinates for each pixel. To generate a 3D reconstruction of the 2D image, a third dimension ($Z_i$) for depth can be predicted/correlated. In some embodiments, the trained CNN 108 may be configured to correspond or correlate each RGB value of each pixel to a depth ($Z_i$) (e.g., a predicted depth) to make the third dimension. This allows conversion of the 2D image into a 3D reconstruction 306 of facial contour as shown in FIG. 3B. Thus, each point on the UV position map can be expressed as:

$$\text{position}(u_i, v_i) = (x_i, y_i, z_i). \quad \text{Eqn. 1}$$

where $u_i$ and $v_i$ represent the X and Y coordinates for any given point, denoted as i, in the 2D UV position map and the RGB values provide depth ($z_i$) information (e.g., generated or predicted by the CNN 108) for each point. In some embodiments, the 3D reconstruction of the face may be provided from the 3D reconstruction module 106 to the visual field prediction module 110 or the 3D reconstruction of the face may be stored in data storage 118.

Figure 4A:
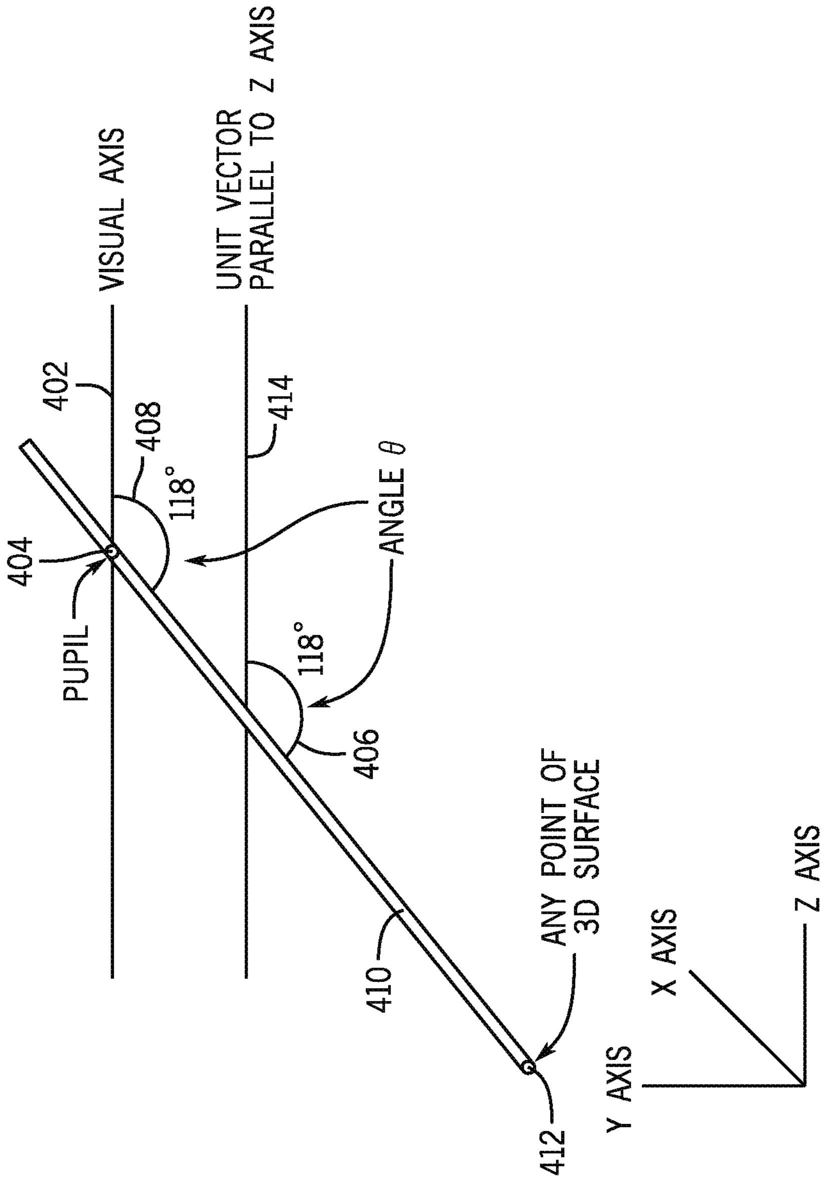
FIG. 4A illustrates the determination of an angle theta (θ) and the coordinates of the points corresponding to a point on a 3D reconstruction of a face of a subject in accordance with an embodiment.

In some embodiments, a visualization of the 3D reconstruction of the subject's face may be generated to be displayed to an operator. The visualization of the 3D reconstruction provides a facial reconstruction model with 3D coordinates for each point originally represented in the UV map. The 3D reconstruction of the subject's face may be used to calculate an angle of intercept between the visual axis and the face following visualization. Referring again to FIG. 2, at block 208, a plurality of angles theta (θ) for the 360° surrounding a visual axis on the 3D reconstruction may be calculated using the visual field prediction module 110. Accordingly, in some embodiments the 3D reconstruction of the face may be provided from the 3D reconstruction module 106 to the visual field prediction module 110 or the 3D reconstruction of the face may be retrieved from data storage 118. In some embodiments, the angles θ may be stored in a data structure. FIG. 4A illustrates the determination of an angle theta (θ) and the coordinates of the points corresponding to a point on a 3D reconstruction of a face of a subject in accordance with an embodiment. To calculate the angles theta (θ), a visual axis may be selected. In some embodiments, the visual axis 402 may be the equal to the center of the pupil 404. As used herein, the angle theta (θ) (e.g., 406, 408 shown in FIG. 4A) is defined as the intersect between a vector 410 from a point 412 on the 3D reconstruction of the subject's face and the visual axis 402. From the reconstruction model, the angle theta (θ) between the visual axis 402 and a plurality of circumferential points surrounding the visual axis 402 on the 3D facial model may be calculated using the trigonometric circle. In some embodiments, the angle theta (θ) may be calculated for all circumferential points (i.e., the 360° surrounding the visual axis 402) on the 3D facial model. In some embodiments, since the angles formed from the intersection of a transverse line with two parallel lines are equal and the visual axis 402 may be parallel to the z-axis (depth coordinate), the unit vector 414 (0i+0j+1k) parallel to the z-axis could be considered the visual axis.

For each vector intersecting points on the reconstructed facial contour and the visual axis 402 (or alternatively unit vector 414), the angle theta may be calculated using the following equation:

$$\cos\theta = \frac{a \cdot b}{\|a\| \cdot \|b\|} \quad \text{Eqn. 2}$$

where a is the unit vector parallel to the visual axis, b is the vector connecting a point on the pupil ($p_1$) to any point ($p_i$) on the face, and θ is the angle of intersection between them. Thus, the vector b will be the difference of $p_i$ ($x_i$,$y_i$,$z_i$) located anywhere on the face, and $p_1$ ($x_1$,$y_1$,$z_1$), located on the pupil, b=($x_i$−$x_1$, $y_i$−$y_1$, $z_i$−$z_1$), $p_i$−$p_1$. Substituting the 3D coordinates into the equation in place of the vectors yields the equation:

$$\cos\theta = \frac{(0 \cdot (x_i - x_1)) + (0 \cdot (y_i - y_1)) + (1 \cdot (z_i) - z_1)}{\sqrt{(x_i - x_1)^2 + (y_i - y_1)^2 + (z_i - z_1)^2} \cdot \sqrt{(0)^2 + (0)^2 + (1)^2}} \quad \text{Eqn. 3}$$

Figure 4B:
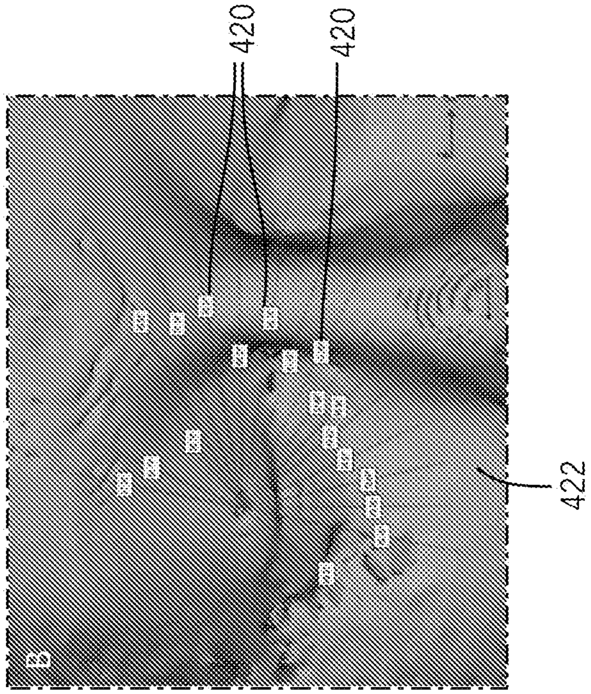
FIG. 4B illustrates a plurality of angles theta (θ) calculated for points circumferential to a visual axis in accordance with an embodiment.

As mentioned, the angle theta (η) may be calculated for all points 420 circumferential to the visual axis on the 3D reconstruction 422 of the face as shown in FIG. 4B. FIG. 4B illustrates a plurality of example angles theta (θ) calculated for points 420 circumferential to the visual axis.

Figure 4C:
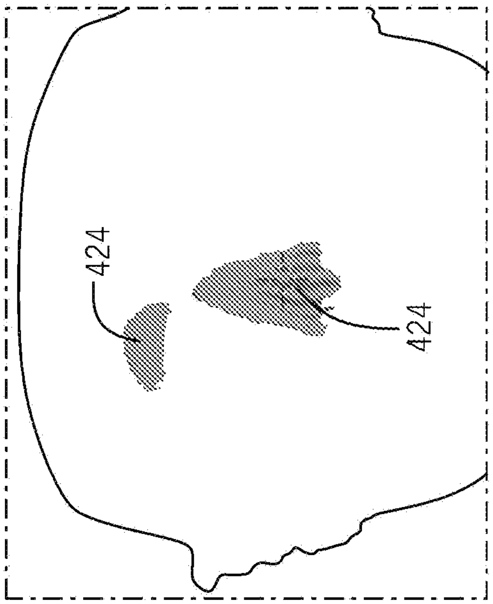
FIG. 4C illustrates an example set of points with an angle theta (θ) less than a predetermine degree in accordance with an embodiment.

Referring to FIG. 2, at block 210, all points in which θ is less than a predetermined or preset angle (or degree) are identified, for example, using the visual field prediction module 110. In some embodiments, the predetermined angle (or degree) may be 60°. In some embodiments, a point with θ less than the predetermined angle, may be predicted to correspond to a visual field defect from facial contours in a visual field pattern. FIG. 4C illustrates an example set of points 424 with an angle theta (θ) less than a predetermined or preset degree, such as, for example, sixty degrees, in accordance with an embodiment.

Figure 4E:
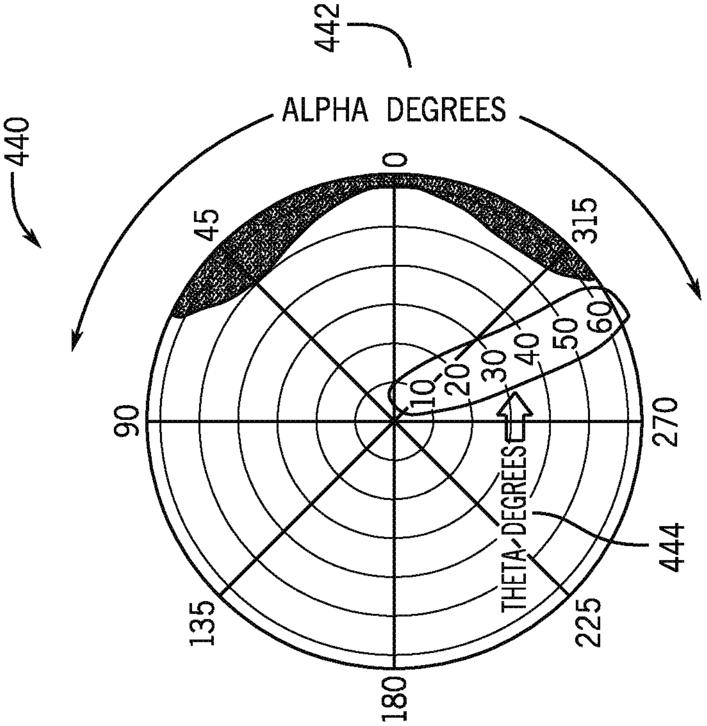
FIG. 4E is an example visual field map (or chart) 440 of a predicted visual field for a subject in accordance with an embodiment.
Figure 4D:
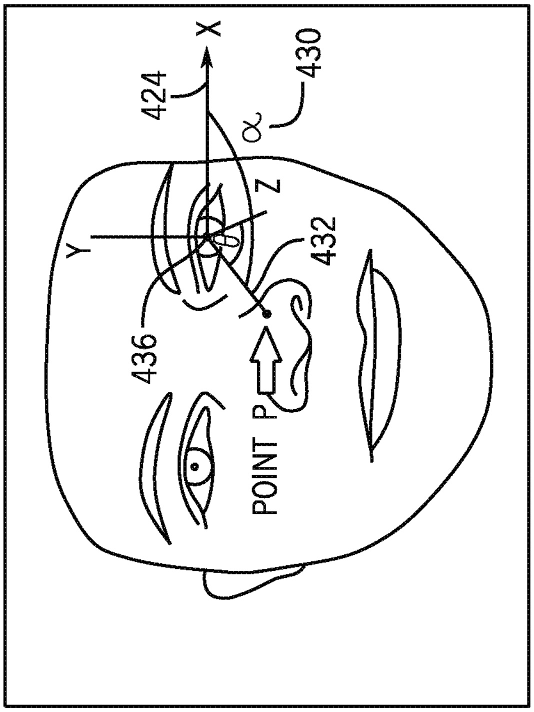
FIG. 4D illustrates the determination of an angle alpha (α) for each point in an example set of points set of points with an angle theta (θ) less than a predetermine degree in accordance with an embodiment.

Referring to FIG. 2, at block 212, a predicted visual field for the subject including predicted visual field defects from facial contours may be generated, for example, using the visual field prediction module 110, based on the plurality of points ($p_i$) where θ is less than the predetermined angle or degree. The predicted visual field may be for a right eye of the subject or a left eye of the subject. For points ($p_i$) where θ is less than the predetermined angle (e.g., 60 degrees), in some embodiments a second angle alpha (α) may be calculated to allow for mapping of the predicted visual defect onto the visual field. FIG. 4D illustrates the determination of an angle alpha (α) for each point in an example set of points with an angle theta (θ) less than a predetermined degree in accordance with an embodiment. In some embodiments, the angle α 430 can correspond to the angle between vector b 432 and unit vector 434 parallel to the x axis. The angle θ 436 and the angle α 430 may then be used for plotting or mapping the points onto a visual field chart (or scatter plot). FIG. 4E is an example visual field map (or chart) 440 of a predicted visual field for a subject in accordance with an embodiment. In FIG. 4E, the alpha angles 442 and theta angles 444 that are used to plot the predicted visual field defects onto the visual field map 440 are shown. In some embodiments, the predicted visual field may be stored in data storage 118.

Referring to FIG. 2, at block 214, an acquired visual field of the subject may be retrieved, for example, from a visual field system 104 or from data storage. The acquired visual field may be for a right eye of the subject or a left eye of the subject. In some embodiments, the acquired visual field may be a 60-4 visual field, although it should be understood that other types of visual fields may be used for the acquired visual field. The acquired visual field may be provided to the visual field correction module 112. At block 216, a corrected visual field for the subject may be generated based on the predicted visual field and the acquired visual field using, for example, the visual field correction module 112. Accordingly, in some embodiments the predicted visual field may be provided from the visual field prediction module 110 to the visual field correction module 112 or the predicted visual field may be retrieved from data storage 118.

Figure 5:
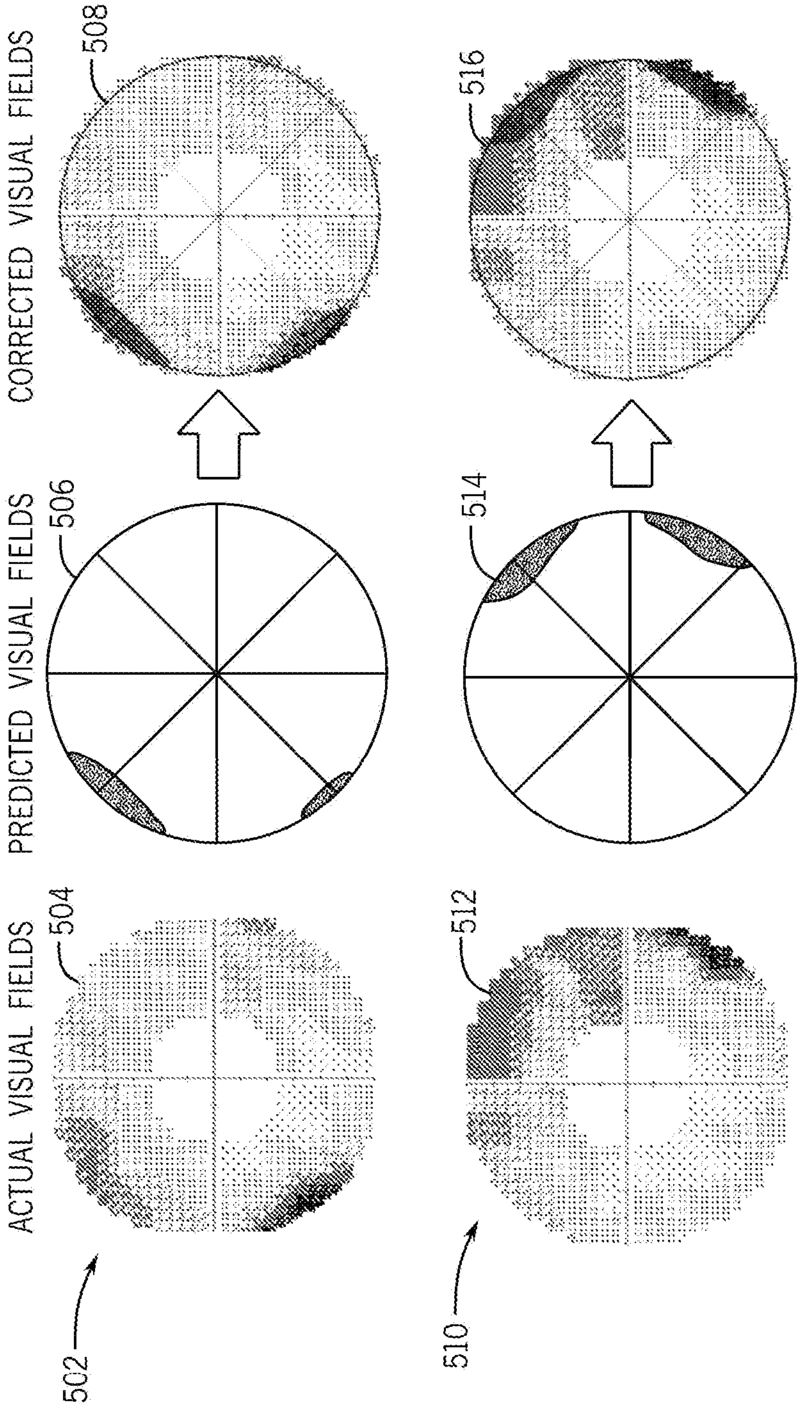
FIG. 5 illustrates an example method for correction of an acquired visual field in accordance with an embodiment.

In some embodiments, a corrected visual field for the subject may be generated by subtracting the predicted visual field from the acquired visual field. For example, the acquired visual field for the subject may be converted to an image and the predicted visual field map for the subject may be converted to an image. The images can be viewed as two concentric circles that may be overlaid on each other. In an embodiment, one of the images may be scaled if necessary so the two images will have the same radius. The corrected visual field may be for a right eye of the subject or a left eye of the subject. In an embodiment, the points that are common in both images may be removed (or subtracted) to eliminate the visual field defects due to facial contour. The subtraction of the predicted visual field will reveal a visual field with only visual field defects due to pathology and remove facial contour visual field defects. FIG. 5 illustrates the correction of an acquired visual field in accordance with an embodiment. In FIG. 5, an acquired (or actual) visual field 504 and a predicted visual field 506 for a first subject 502 and an acquired (or actual) visual field 512 and a predicted visual field 514 for a second subject are shown. For the first subject 502, a corrected visual field 508 may be generated by subtracting the predicted visual field 506 from the acquired visual field 504 (e.g., by removing the points (i.e., visual field defects) in common between the acquired 504 and predicted 506 visual fields). For the second subject 510, a corrected visual field 516 may be generated by subtracting the predicted visual field 514 from the acquired visual field 512 (e.g., by removing the points (i.e., visual field defects) in common between the acquired 512 and predicted 514 visual fields).

Figure 6A:
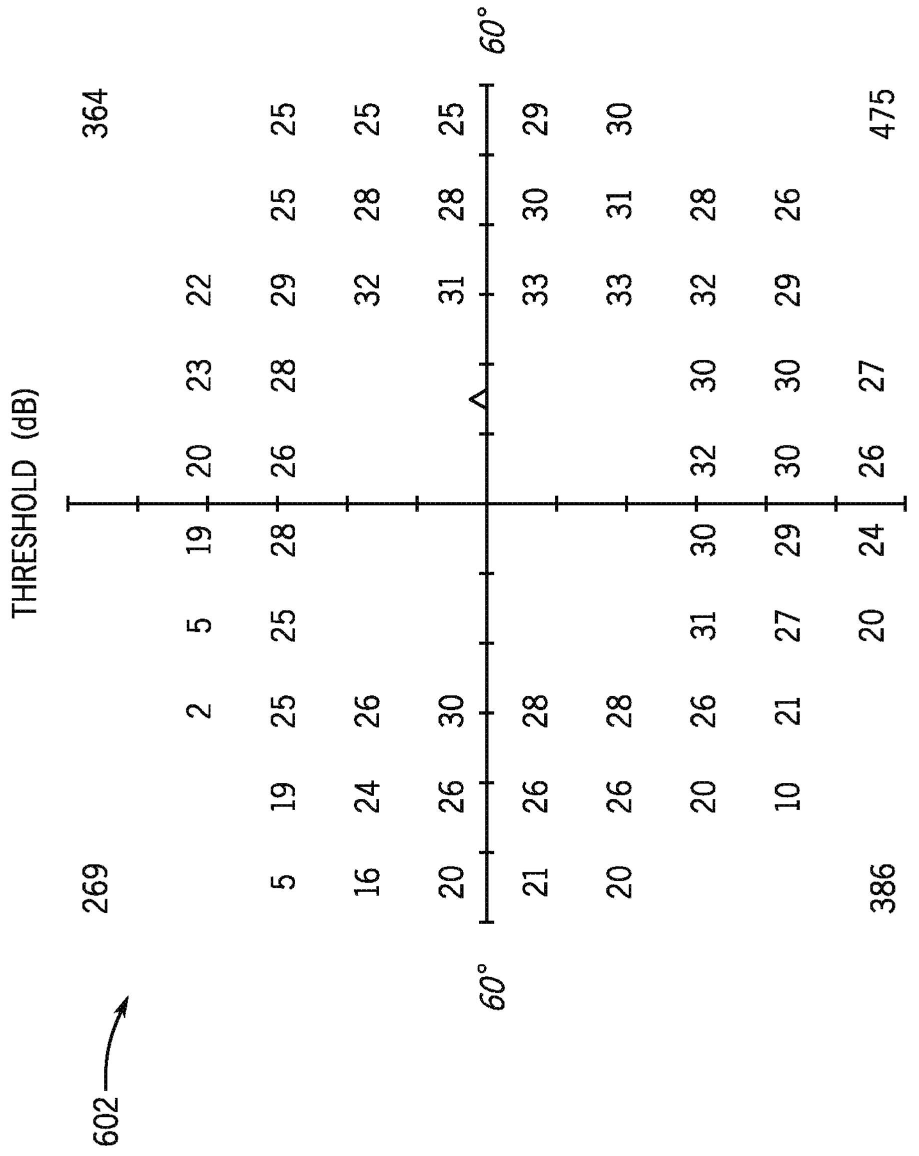
Figure 6B:
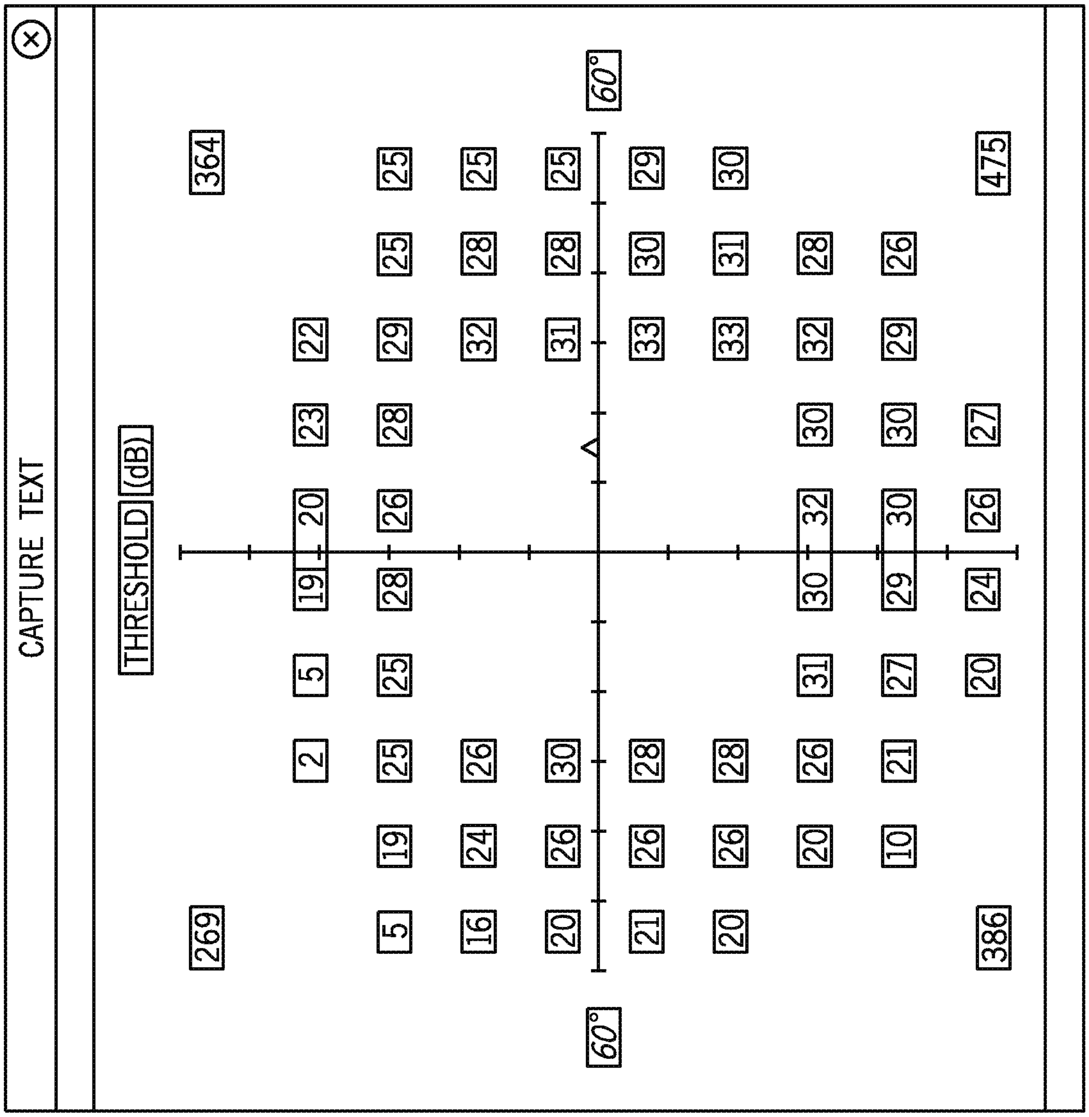

Alternatively, in some embodiments, the corrected visual field may be generated at block 216 using a numerical correction method. FIGS. 6A-6E illustrate an example numerical method for correction of an acquired visual field in accordance with an embodiment. In the example numerical correction method, optical character recognition (OCR) (e.g., performed using an OCR process or system) may be used to automate the process of numerical correction. As discussed further below, numbers for threshold values for an acquired visual field may be recognized using OCR and the acquired visual field may be corrected numerically. In some embodiments, the acquired visual field image may be pre-processed to improve the accuracy (e.g. so that the acquired visual field may be properly recognized using OCR). In some embodiments, the preprocessing may include cropping the acquired visual field image. In some embodiments, the preprocessing may also include converting the visual field image to grayscale/black and white. In some embodiments, the visual field image may then be converted to a binary image by thresholding to make the white pixels maximum white and the black pixels maximum black to eliminate any noise on the visual field image to improve the accuracy of character (or threshold value) detection on the acquire visual field. FIG. 6A illustrates an example visual field image 602 after applying the threshold function (referred to herein as a threshold image of the acquired visual field). OCR may then be used to detect the characters, threshold values and a summation of the threshold values in each quadrant of the visual field. FIG. 6B illustrates an example OCR 604 of the visual field image (or threshold image) 602 in FIG. 6A. In the illustrated example, the characters with a rectangle around them have been detected using OCR. The detected characters may be accessed by, for example, a processor performing the method for correcting a visual field and implementing the visual field correction module 112. FIG. 6C illustrates an example set of characters 606 from FIG. 6B that have been recognized using OCR. The numbers that have been accessed may be used for further calculations of the numerical correction process using, for example, the visual field correction module 112. In addition, a summation of the thresholds of each quadrant of the visual field image may also be accessed and used in the numerical correction process by the visual field correction module 112.

Figure 6D:
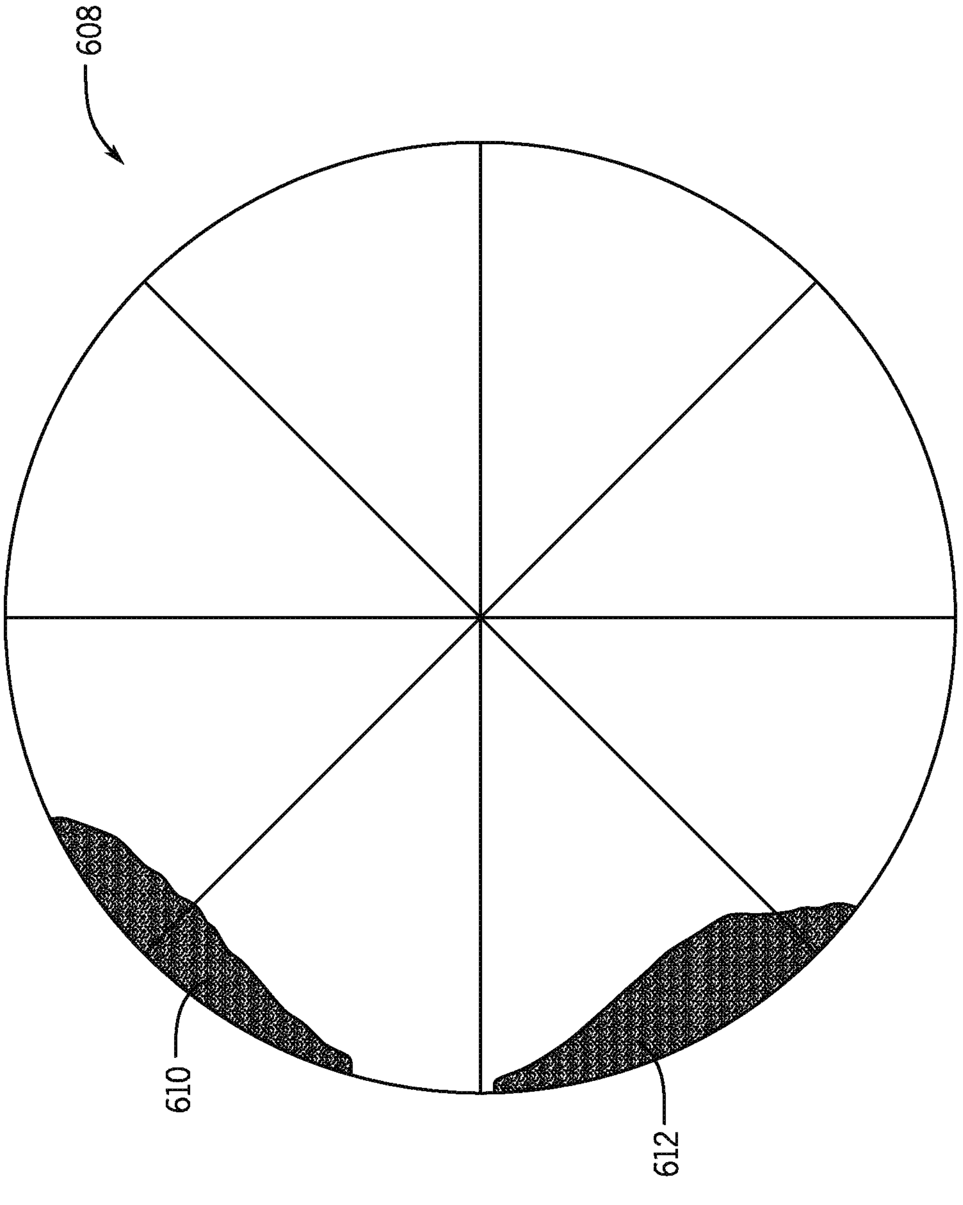
Figure 6E:
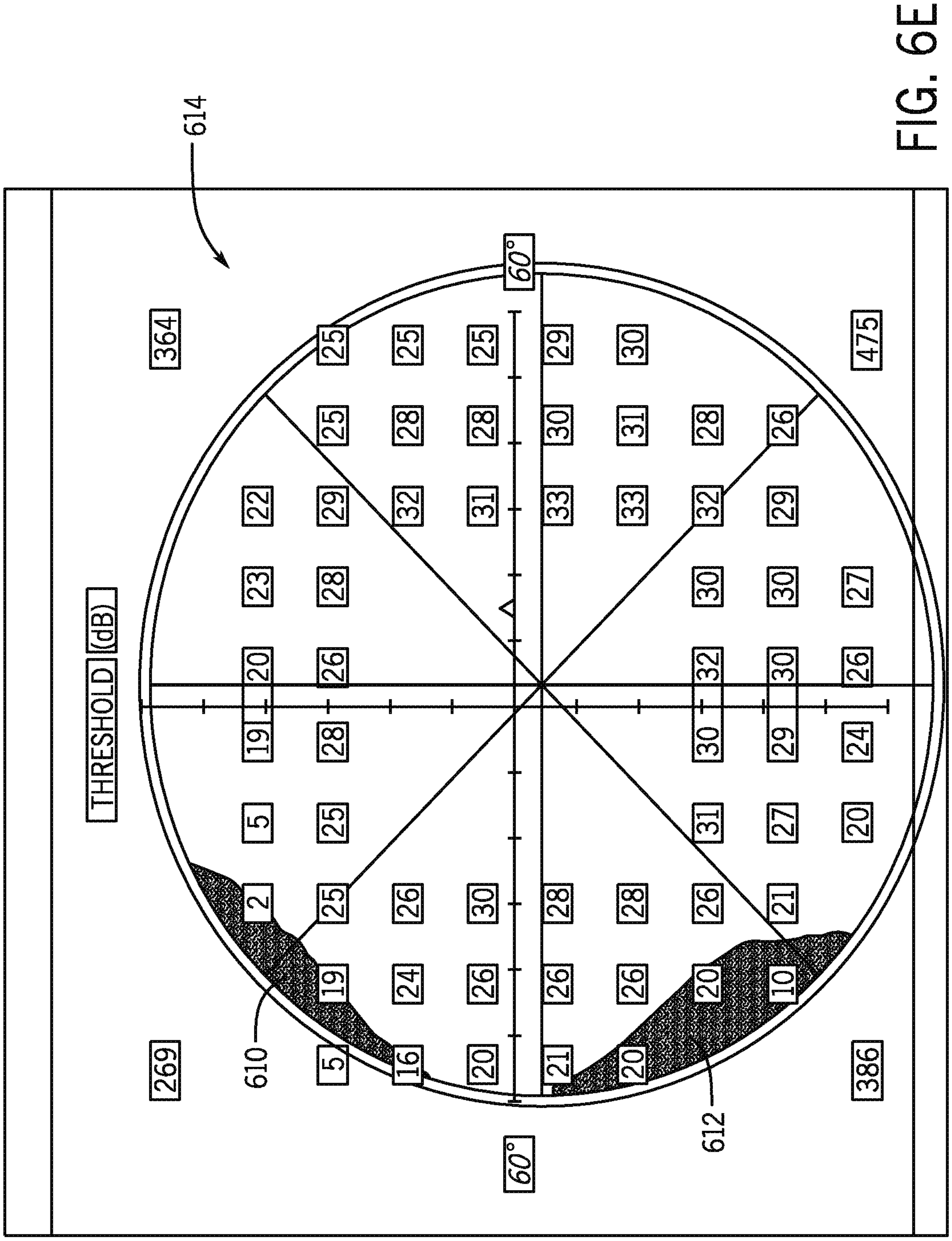

The predicted visual field image (as generated at block 212) may be mapped onto the threshold image 602 (shown in FIG. 6A) of the acquired visual field and the numbers of the threshold image 602 that are covered by the predicted visual field image may be set to zero. FIG. 6D illustrates an example predicted visual field image 608 that represents the visual field defects due to facial anatomy. In FIG. 6D, the regions 610 and 612 show the visual field defects. FIG. 6E illustrates an example of a mapping 614 of the predicted visual field image 608 onto the threshold image 602 of the acquired visual field. After mapping the predicted visual field image 608 on the threshold image 602, in some embodiments the detected threshold numbers (e.g., detected using OCR) that correspond to the predicted visual field can be set equal to zero. In some embodiments, this may be implemented by detecting the numbers that are present in the regions 610 and 612 that correspond to the visual field defects from the predicted visual field image. The numbers that are present in the region 610 and 612 may be changed to zero and the summation of the numbers will be subtracted from the summation of all threshold values at each quadrant. Accordingly, the threshold values that correspond to the predicted visual field defects due to facial structure (e.g., represented by regions 610, 612) may be equal to zero and the summation of the thresholds may be corrected. Using the method described above with respect to FIGS. 6A-6E, the acquired visual field may be corrected numerically.

Figure 9:
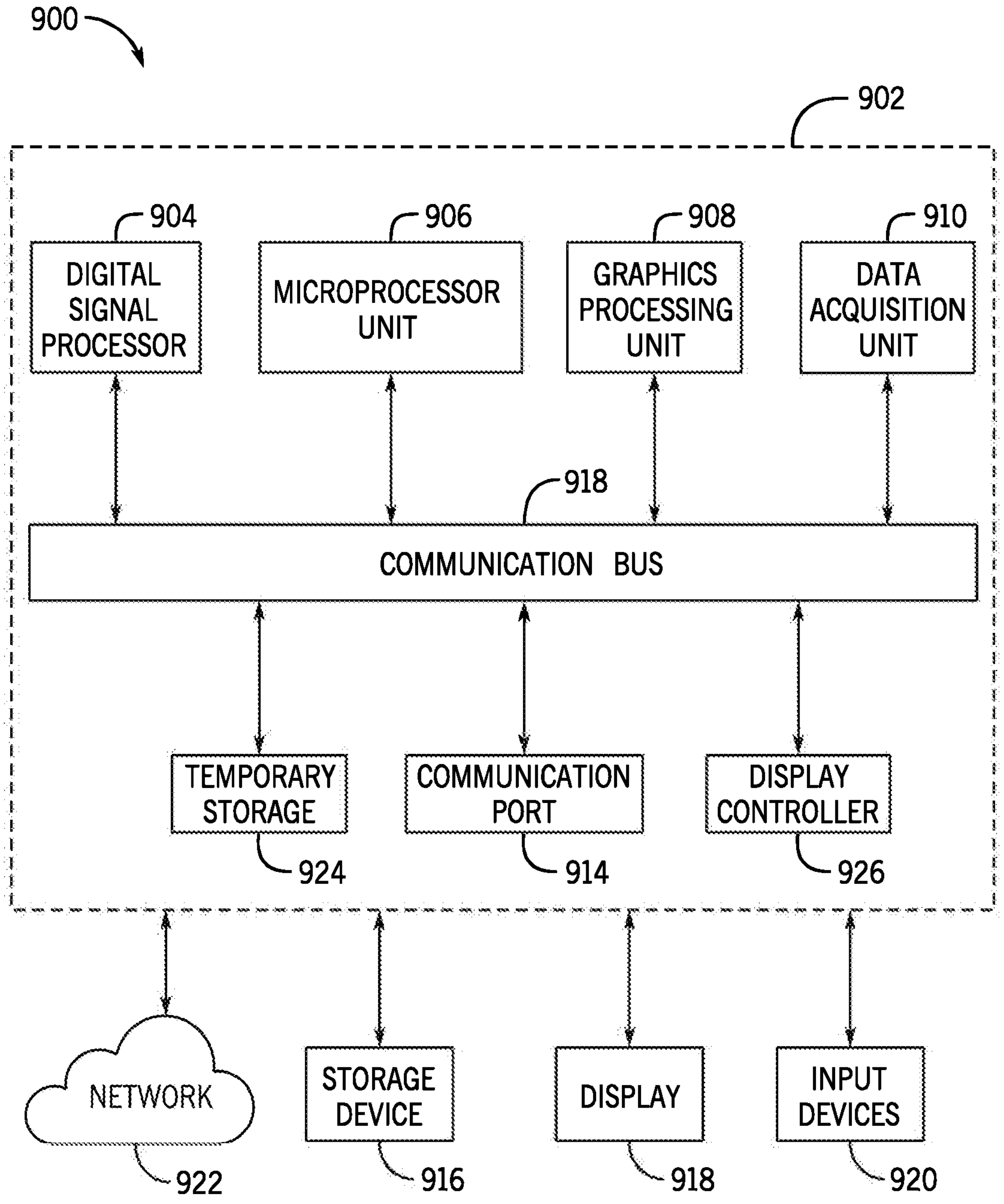
FIG. 9 is a block diagram of an example computer system in accordance with an embodiment.

Referring again to FIG. 2, at block 218, the corrected visual field may be displayed on a display, for example, a display on a visual field system 104, or other computer system (e.g., display 918 of computer system 900 shown in FIG. 9). In some embodiments, the corrected visual field may be stored in data storage 118.

Figure 7A:
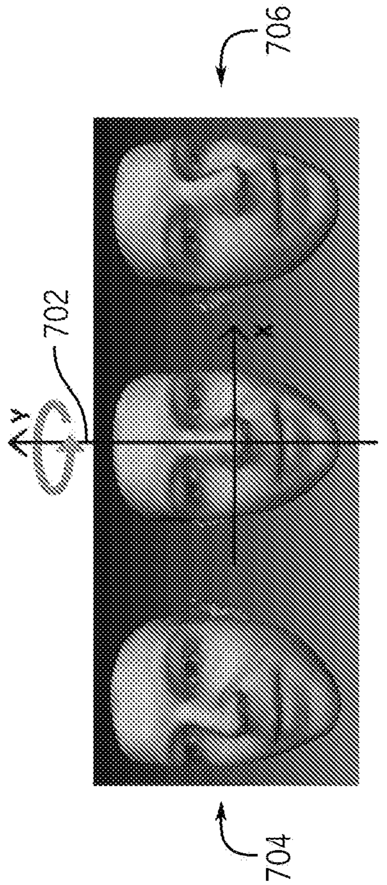
FIG. 7A illustrates an example head turn (or rotation) about a vertical axis in accordance with an embodiment.

Visual field defects related to the face contour may be changed or altered if the subject's head is turned in the visual field system. For example, an optimal head position (e.g., turning the head to an optimal head turn angle) in the visual field system may be used to maximize the visual field of the subject. The amount of head turn to maximize the visual field for each individual can be different. FIG. 7A illustrates an example head turn (or rotation) about a vertical axis in accordance with an embodiment. In FIG. 7A, a first head turn 704 is shown about a vertical axis 702 to the right and a second head turn 706 is shown to the left. As used herein, the head turn angle may be defined as the amount of turning or rotation of the head about the vertical axis 702. The head turn may be either toward (i.e., temporally) or away from (i.e., nasally) the tested eye.

Figure 7B:
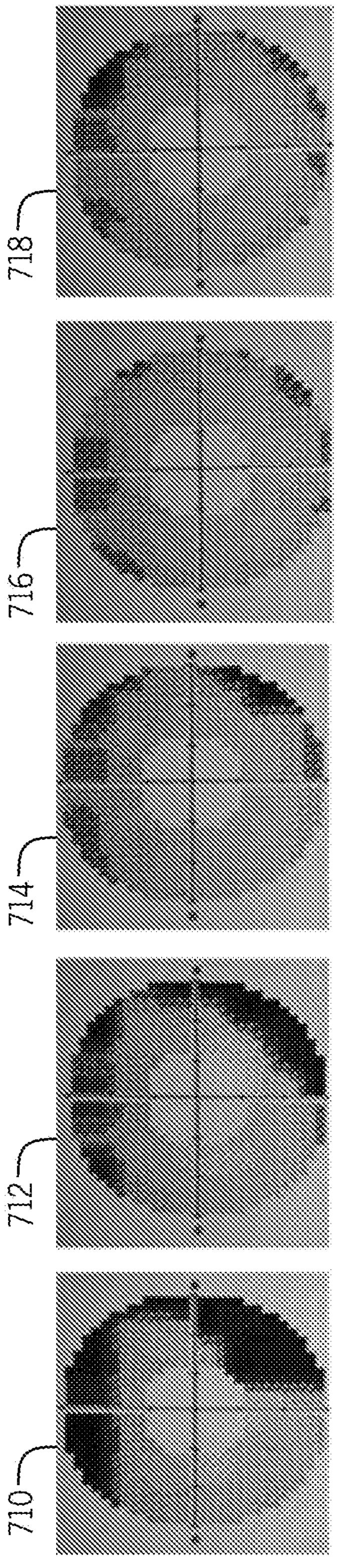
FIG. 7B illustrates an example series of visual field maps for a subject showing the effect of turning the head of the subject in accordance with an embodiment.

FIG. 7B illustrates an example series of visual field maps for a subject showing the effect of turning the head of the subject in accordance with an embodiment. In the example of FIG. 7B, the visual field maps 710, 712, 714, 716 and 718 are 60-4 visual fields. In FIG. 7B, each visual field map 710, 712, 714, 716 and 718 represents a different head position 5 or head turn angle for the subject. In this example, visual field map 710 represents a 25-30° head turn toward (i.e., temporally) the eye being tested. Visual field map 712 represents a 10-15° head turn toward the eye being tested. Visual field map 714 represents the head in a primary position (i.e., no head turn). Visual field map 716 represents a 10-15° head turn away from (i.e., nasally) the tested eye. Visual field map 718 represents a 25-30° head turn away from the tested eye. In the example shown in FIG. 7B, the visual field defects decreased when the head was turned away from the tested eye and the visual field defects increased when the head was turned towards the tested eye. By turning the head about the vertical axis 702 (shown in FIG. 7A) in the opposite direction from the tested eye, the tested eye is abducted when fixating on the central target, and therefore the influence of the nose on the nasal visual field is minimized. Accordingly, the subject has a more accurate visual field when the head was turned away from the tested eye. As mentioned, the amount of head turn to maximize the visual field for each individual is different.

Figure 8:
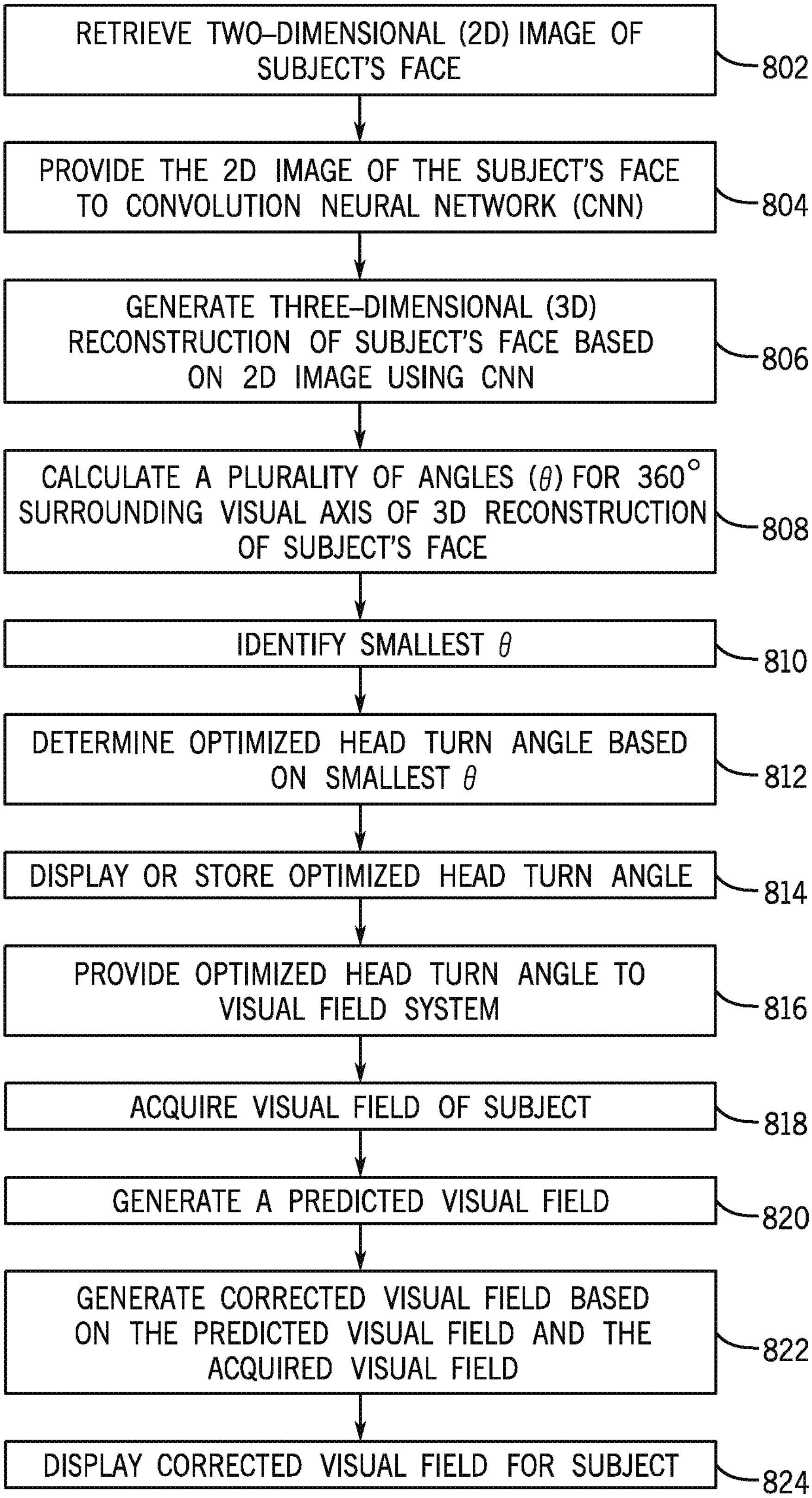
FIG. 8 illustrates a method for determining and optimizing a head turn of a subject for a visual field test and determining a corrected visual field for the subject in accordance with an embodiment.

FIG. 8 illustrates a method for determining and optimizing a head turn of a subject for a visual field test and determining a corrected visual field for the subject in accordance with an embodiment. The process illustrated in FIG. 8 is described below as being carried out by the system 100 for correcting and optimizing a visual field of a subject as illustrated in FIG. 1. Although the blocks of the process are illustrated in a particular order, in some embodiments, one or more blocks may be executed in a different order than illustrated in FIG. 8, or may be bypassed.

In some embodiments, an optimized head turn angle may be determined based on a 3D reconstruction of the face of a subject. The 3D reconstruction may be generated at block 802-806 from a 2D image of the face of the subject in a similar manner as described above with respect to blocks 202-206 of FIG. 2, for example, using the 3D reconstruction module 106. The 3D reconstruction of the face may be provided from the 3D reconstruction module 106 to the visual field prediction module 110 or the 3D reconstruction of the face may be stored in data storage 118. In addition, at block 808, a plurality of angles theta (θ) for the 360° surrounding a visual axis on the 3D reconstruction may be calculated using the visual field prediction module 110 or the head turn optimization module 114 using similar methods as described above with respect to FIGS. 2 and 4A. Accordingly, the angle theta (θ) may be calculated for a plurality of points circumferential to a visual axis on the 3D reconstruction of the face. In some embodiments, the angle theta (θ) may be calculated for all circumferential points (i.e., the 360° surrounding the visual axis) on the 3D facial model. In an embodiment, the angles θ along with the coordinates of the points may be stored in a data structure. The plurality of angles theta (θ) may be stored in data storage 118. At block 810, the smallest (or minimum) angle theta may be identified (e.g., using the head turn optimization module 114) from the angles theta calculated at block 808. At block 812, an optimal head turn angle, K, may be determined based on the smallest angle θ using the head turn angle optimization module 114. As mentioned above, the head turn angle may be defined as the amount of turning or rotation of the head about a vertical axis. The head turn may be either toward (i.e., temporally) or away from (i.e., nasally) the tested eye. In some embodiments, the optimal head turn angle, K, is determined by subtracting the smallest angle θ from a preset angle (e.g., 60 degrees). In some embodiments, at block 814, the optimal head turn angle may be displayed on a monitor or display to an operator (e.g., a display of the visual field system 102 or display 918 of computer system, 900 shown in FIG. 9) or stored in data storage 118.

At block 816, the optimal head turn angle may be provided to a visual field system 104. In some embodiments, an operator may then position the subject's head at the optimal angle in the visual field system and perform a visual field test using the visual field system to acquire a visual field of the subject at block 818. By adjusting the head with, for example, turning and tilting, the facial anatomy can be overcome and the maximal far peripheral field can be mapped. Once the visual field has been acquired with the subject's head at the optimal position determined at block 812, in some embodiments the acquired visual field at the optimal head position may be corrected to eliminate any residual facial contour visual field defects. For example, at block 820 a predicted visual field may be generated using the visual field prediction module 110 in a similar manner as described above with respect to blocks 210-212 of FIG. 2. At block 822, a corrected visual field may be generated based on the predicted visual field and the acquired visual field using the visual field correction module 112 in a similar manner as described above with respect to block 216 of FIG. 2.

In some embodiments, at block 818 a first visual field of the subject may be acquired at the primary head position and a second visual field of the subject may be acquired at the optimal head position determined at block 812. In this example, the first visual field at the primary head position may be corrected to remove facial contour visual field defects and the second visual field at the optimal head position may be corrected to remove facial contour visual field defects. As mentioned, a predicted visual field may be generated at block 820 in a similar manner as described above with respect to blocks 210-212 of FIG. 2 and the corrected first visual field and a corrected second visual field may be generated at block 822 based on the predicted visual field and the acquired visual field in a similar manner as described above with respect to block 216 of FIG. 2.

In some embodiments, a visual field of the subject may be acquired at block 818 at the primary head position and the visual field system may be configured to project stimuli in an optimal area based on the optimal head position determined at block 812. The acquired visual field at the primary head position may then be corrected to remove any residual facial contour visual field defects. As mentioned, a predicted visual field may be generated at block 820 in a similar manner as described above with respect to blocks 210-212 of FIG. 2 and the corrected visual field may be generated at block 822 based on the predicted visual field and the acquired visual field in a similar manner as described above with respect to block 216 of FIG. 2.

In some embodiments, a first portion of a visual field of the subject may be acquired at block 818 at the optimal head position determined at block 812 and a second (or remaining) portion of the visual field of the subject may be acquired at the primary head position. The acquired visual field (with a first portion at the primary head position and a second portion at the optimal head position) may then be corrected to remove any facial contour visual field defects. As mentioned, a predicted visual field may be generated at block 820 in a similar manner as described above with respect to blocks 210-212 of FIG. 2 and the corrected visual field may be generated at block 822 based on the predicted visual field and the acquired visual field in a similar manner as described above with respect to block 216 of FIG. 2.

At block 824, the corrected visual field may be displayed on a display, for example, a display on a visual field system 104, or other computer system (e.g., display 918 of computer system 900 shown in FIG. 9). In some embodiments, the corrected visual field may be stored in data storage 118.

FIG. 9 is a block diagram of an example computer system in accordance with an embodiment. Computer system 900 may be used to implement the systems and methods described herein. In some embodiments, the computer system 900 may be a workstation, a notebook computer, a tablet device, a mobile device, a multimedia device, a network server, a mainframe, one or more controllers, one or more microcontrollers, or any other general-purpose or application-specific computing device. The computer system 900 may operate autonomously or semi-autonomously, or may read executable software instructions from the memory or storage device 916 or a computer-readable medium (e.g., a hard drive, a CD-ROM, flash memory), or may receive instructions via the input device 920 from a user, or any other source logically connected to a computer or device, such as another networked computer or server. Thus, in some embodiments, the computer system 900 can also include any suitable device for reading computer-readable storage media.

Data, such as data acquired with, for example, a visual field system or a camera, may be provided to the computer system 900 from a data storage device 916, and these data are received in a processing unit 902. In some embodiment, the processing unit 902 includes one or more processors. For example, the processing unit 902 may include one or more of a digital signal processor (DSP) 904, a microprocessor unit (MPU) 906, and a graphics processing unit (GPU) 908. The processing unit 902 also includes a data acquisition unit 910 that may be configured to electronically receive data to be processed. The DSP 904, MPU 906, GPU 908, and data acquisition unit 910 are all coupled to a communication bus 912. The communication bus 912 may be, for example, a group of wires, or a hardware used for switching data between the peripherals or between any component in the processing unit 902.

The processing unit 902 may also include a communication port 914 in electronic communication with other devices, which may include a storage device 916, a display 918, and one or more input devices 920. Examples of an input device 920 include, but are not limited to, a keyboard, a mouse, and a touch screen through which a user can provide an input. The storage device 916 may be configured to store data, which may include data such as, for example, acquired data, acquired visual fields, 2D images of a face of a subject, 3D reconstructions of the face of a subject, predicted visual fields, corrected visual fields, optimal head turn angle, etc., whether these data are provided to, or processed by, the processing unit 902. The display 918 may be used to display images and other information, such as patient health data, and so on.

The processing unit 902 can also be in electronic communication with a network 922 to transmit and receive data and other information. The communication port 914 can also be coupled to the processing unit 902 through a switched central resource, for example the communication bus 912. The processing unit can also include temporary storage 924 and a display controller 926. The temporary storage 924 may be configured to store temporary information. For example, the temporary storage 924 can be a random access memory.

Computer-executable instructions for generating a 3D reconstruction of a face of a subject, correcting a visual field of a subject and determining an optimal head turn angle for a visual field according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present disclosure has described one or more preferred embodiments, and it should be appreciated that many equivalents, alternatives, variations, and modifications, aside from those expressly stated, are possible and within the scope of the invention.

The invention claimed is:

1. A system for determining a visual field of a subject, the system comprising:

a three dimensional (3D) reconstruction module configured to receive a two-dimensional (2D) image of a face of the subject and comprising a convolutional neural network configured to generate a 3D reconstruction of the face of the subject based on the 2D image of the face of the subject;

a visual field prediction module coupled to the 3D reconstruction module and configured to generate a predicted visual field for the subject based on the 3D reconstruction of the face of the subject; and a visual field correction module coupled to the visual field prediction module and configured to receive a visual field for the subject acquired using a visual field system, the visual field correction module further configured to generate a corrected visual field based on the predicted visual field for the subject and the acquired visual field for the subject.

2. The system according to claim 1, wherein the visual field prediction module is further configured to:

determine a plurality of intersect angles between a visual axis and a plurality of circumferential points on the 3D reconstruction of the face of the subject;

identify a set of circumferential points with a corresponding intersect angle less than a predetermined angle; and generate the predicted visual field for the subject based on the set of circumferential points with a corresponding intersect angle less than the predetermined angle.

3. The system according to claim 1, wherein generating a corrected visual field comprises subtracting the predicted visual field from the acquired visual field.

4. The system according to claim 1, wherein generating a corrected visual field comprises a numerical correction of the acquired visual field based on the predicted visual field.

5. The system according to claim 1, wherein the 2D image of the face of the subject is a photograph.

6. The system according to claim 1, wherein the 2D image of the face of the subject is acquired using a camera.

* * * * *